United States Patent [19]

Marshall

[11] Patent Number: 4,483,675
[45] Date of Patent: Nov. 20, 1984

[54] PRODUCTION OF TUBES FOR DENTAL IMPRESSIONS

[76] Inventor: Kenneth H. Marshall, 85 The Bulwark, Castlecrag, Australia, 2068

[21] Appl. No.: 459,635

[22] PCT Filed: May 7, 1982

[86] PCT No.: PCT/AU82/00068
§ 371 Date: Dec. 22, 1982
§ 102(e) Date: Dec. 22, 1982

[87] PCT Pub. No.: WO82/03762
PCT Pub. Date: Nov. 11, 1982

[30] Foreign Application Priority Data

May 7, 1981 [AU] Australia ............................... PE8751
Mar. 12, 1982 [AU] Australia ............................... PF3090

[51] Int. Cl.³ .............................................. A61C 3/00
[52] U.S. Cl. ........................................ 433/141; 433/40
[58] Field of Search ............................ 433/40, 36, 141

[56] References Cited

U.S. PATENT DOCUMENTS

| | | | |
|---|---|---|---|
| 1,812,008 | 6/1931 | Lace | 433/40 |
| 2,349,607 | 5/1944 | Berger | 433/40 |
| 3,390,458 | 12/1968 | Cohen | 433/40 |
| 3,548,500 | 7/1968 | Lytton | 433/40 |
| 3,686,754 | 8/1972 | Kondoloff | 433/40 |
| 4,255,140 | 3/1981 | Marshall | 433/40 |

*Primary Examiner*—Robert Peshock
*Attorney, Agent, or Firm*—Ladas & Parry

[57] ABSTRACT

Method and means for obtaining a dental impression of a reduced tooth for jacket crown, bridgework and like constructions, comprising the use of an impression tube which is substantially inflexible at least longitudinally and which is attached to a syringe for supply of impression material when placed about a tooth and which has a distal end provided with a contour corresponding to the gingival margin at said tooth by the scribing on said tube of a line substantially parallel to the gingival margin, and subsequently removing the end portion of the tube beyond said line.

5 Claims, 6 Drawing Figures

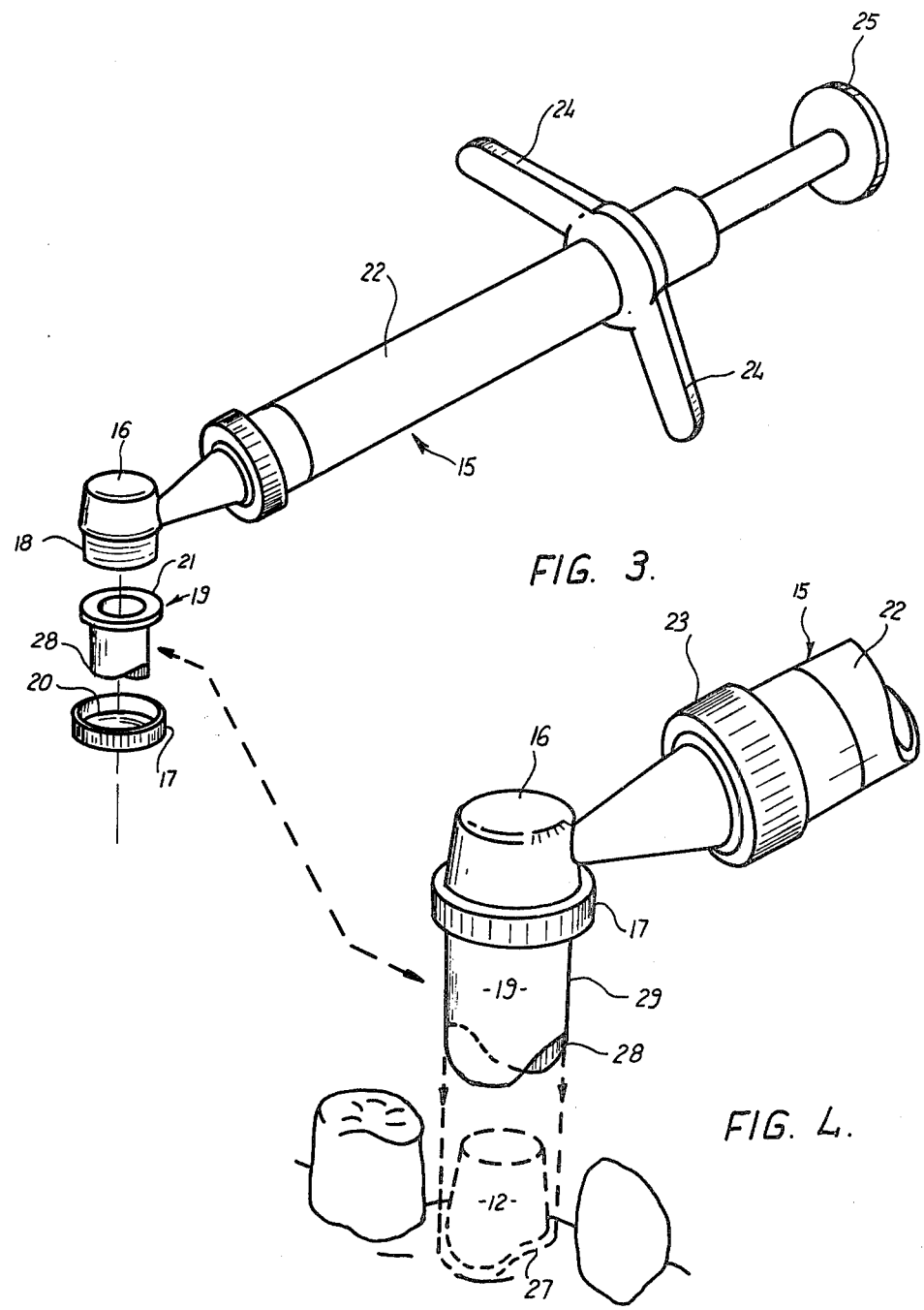

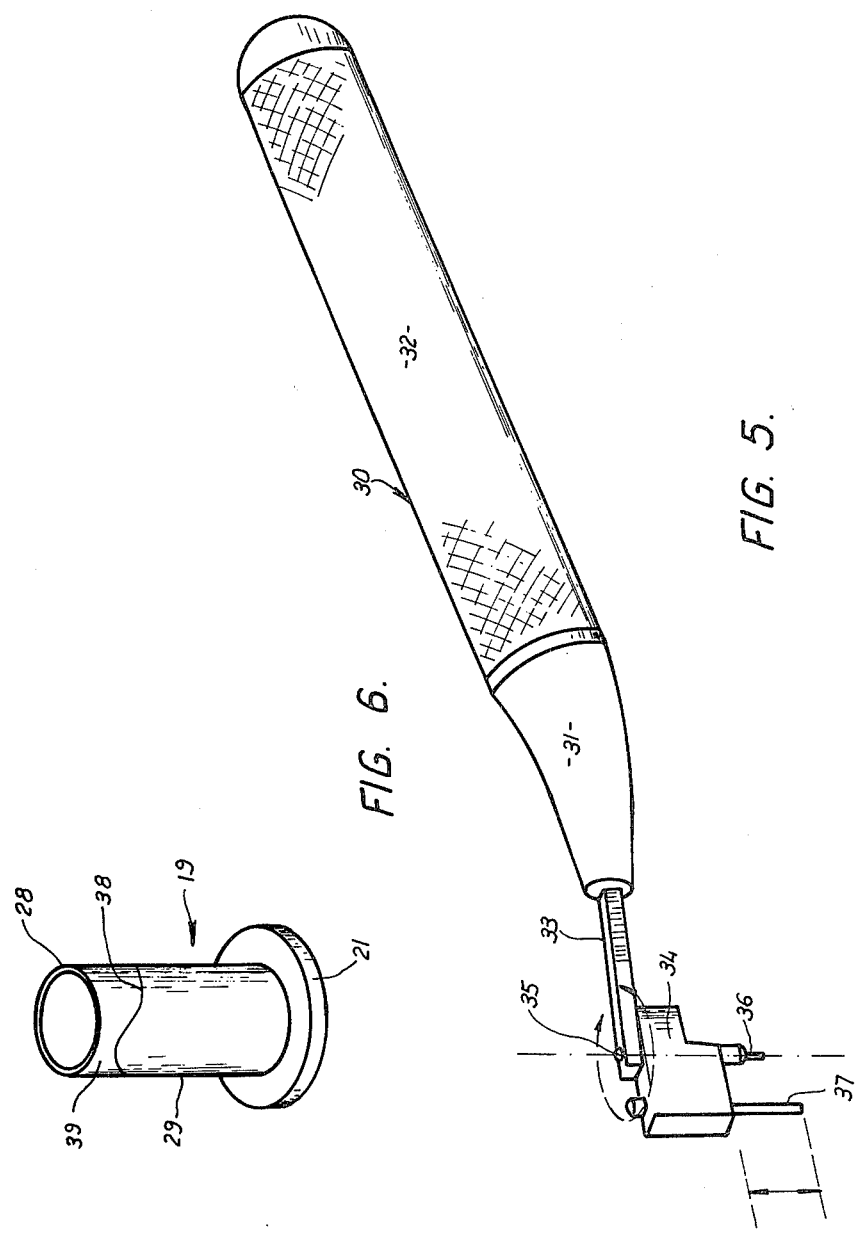

PRODUCTION OF TUBES FOR DENTAL IMPRESSIONS

The present invention relates to the preparation of dental impressions of teeth prepared for the fitting of jacket crowns and bridgework, and more particularly to the production of tubes for use in preparing such impressions.

BACKGROUND ART

Tooth reduction in the preparation for the fitting of a jacket crown involves circumferential reduction of the tooth which includes the creation of a subgingival shoulder which is uniformly recessed within the gingival sulcus. Correct fitting of the crown to the tooth requires the production of a dental impression of the tooth including its subgingival configuration.

Several methods are presently used to retract the gingival tissue disposed outwardly of its attachment to the tooth for access by the impression material into the gingival sulcus. In some cases tissue is removed by surgical means and in other instances this is achieved by chemically impregnated retraction strings, or cords, packed into the sulcus. In the former methods damage sometimes occurs to the underlying vascular and connective tissue which will prevent full regeneration of the gingiva. In the latter instances laceration of the tissue can occur and patient reaction to the chemicals is not always favourable.

It has already been proposed by U.S. Pat. No. 4,074,436 to secure in an impression tray inflexible tubes of copper, or the like, at the position of the reduced tooth or teeth. In that instance the distal end of the tube is pre-contoured to the gingival margin. After the tray filled with impression material, has been applied to the jaw of the patient further impression material is applied by a syringe down the copper tube, or tubes, to surround the reduced tooth and penetrate to its subgingival shoulder. The use of these tubes does not require retraction of the gingival tissue but, however, due to the difficulties in matching the contour of the distal end of the tubes to the gingival margin of the tooth and of precisely positioning the tubes in the tray, the services of a dental technician in his own laboratory are necessary. Resulting inconvenience to the dental surgeon and to the patient therefore occurs.

In U.S. Pat. No. 4,255,140 a solution to these problems is proposed by utilizing a flexible tube which is attached to the end of a syringe containing impression material. The outer end of the tube requires to be generally contoured to the gingival margin, which is selected from a stock, and is forced down into the gingival crevasse as impression material is exuded from the syringe as the tube is withdrawn from the tooth. A loaded impression tray is then applied over the deposited material about the tooth. Reliance is placed upon the longitudinal resiliency in the tube to enable its outer end to enter the gingival crevasse without injury to the gingival attachment. Two principal drawbacks have been found with this proposal, firstly the difficulty of the dentist readily obtaining a reasonably accurate contour on the tube, and secondly due to the flexibility of the tube it becomes far too floppy and unmanageable under pressurized conditions of use.

DISCLOSURE OF INVENTION

It is the object of this invention to improve the procedure for obtaining a dental impression of a tooth reduced for crown or bridge construction which substantially avoids the above-noted drawbacks.

In one general form the invention provides in a method for obtaining a dental impression of a reduced tooth for jacket crown, bridgework or the like construction, which includes providing a tube having an internal diameter substantially corresponding to the diameter of the gingival sulcus in respect of the reduced tooth and having an end contoured to the shape of the gingival margin of the reduced tooth, attaching the opposite end of the tube about the nozzle of a syringe containing impression material, axially applying the tube over the reduced tooth so that its contoured end protrudes into the gingival sulcus of the said reduced tooth, applying impression material from the syringe through said tube until said material exudes from around the contoured end of the tube, retracting said tube while continuing to apply impression material from said syringe until the tube is entirely withdrawn from the reduced tooth, applying a mass of impression material carried in an impression tray over the patients jaw including said reduced tooth, and removing the entire impression material from the patients mouth by withdrawing the impression tray after setting of the impression material, the improvement of providing said tube of a material and thickness to be at least axially substantially inflexible, and of firstly scribing thereon a line parallel to said gingival margin while positioning the tube over the reduced tooth and subsequently trimming the end of said tube to said line to form an accurately contoured end on said tube.

According to specific embodiments of the invention the tube may be of entirely inflexible material, such as copper, or it may be of any suitable synthetic resinous material of determined thickness such that it is axially substantially inflexible but capable of deformation transversely. The distal contour thereon is obtained by axially applying a tube of selected internal diameter over the reduced tooth until the distal end thereof engages a prominent part of the gingiva, scribing a line parallel with the gingival margin on a portion of the exterior wall of the tube spaced from its distal end, then withdrawing the tube from the tooth and removing the end portion of the tube beyond the scribed line.

In another general form of the invention there is provided a receptacle for dental impression material, and comprising a tubular body axially substantially inflexible and readily deformable in cross section, and an outwardly projective annular end flange integrally formed with said body and of thickened material to be substantially inflexible for mounting of said receptacle.

Also the invention provides an instrument for scribing a line on a dental tube, and comprising a contra-angle handpiece of the kind hereinbefore defined, and a head rotatable with respect to the handpiece on an axis in substantially a common plane with the two arms of said handpiece, and supporting a sprung tracing pin and a spaced stylus.

Furthermore, the invention provides a method of forming on an end of a dental impression tube a contour substantially corresponding to the gingival margin of a tooth, and comprising locating the tube over the tooth and adjacent the gingiva, scribing a line on the outer wall of the tube which is substantially parallel with the gingival margin, and removing from the tube that portion of its end beyond said scribed line.

BRIEF DESCRIPTION OF DRAWINGS

The invention will be better understood from the following description read in conjunction with the accompanying drawings, in which:

FIG. 3 shows a form of syringe for mounting of an impression tube of this invention;

FIG. 4 depicts the application of a contoured tube mounted in the syringe to a patient's reduced tooth;

FIG. 5 shows a conventional dental contra-angle hand-piece modified to serve as a scribing instrument for and impression tube; and FIG. 6 depicts an impression tube, of a preferred form, before use.

BEST MODE OF CARRYING OUT INVENTION

Figure 1:
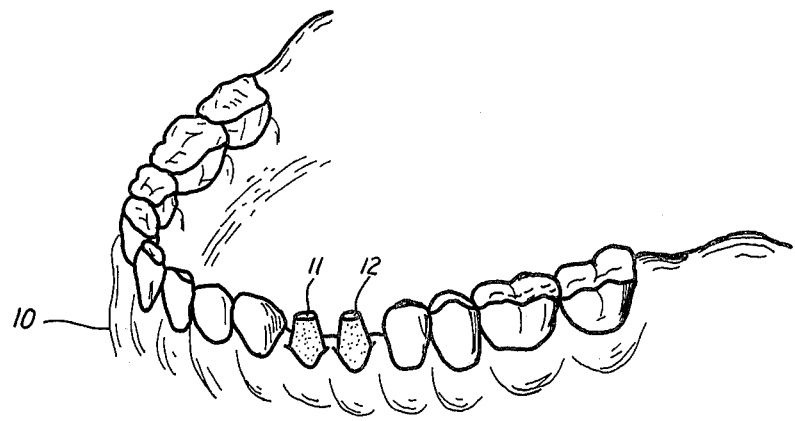
FIG. 1 depicts a lower jaw of a patient on which two incisors have been reduced in preparation for the fitting of jacket crowns.

Referring now to FIG. 1, there is illustrated a lower jaw 10 of a human patient in which tooth 11 and tooth 12 have been reduced in preparation for a jacket crown. Reduction of the teeth is accomplished in any conventional manner to include slightly tapering walls. The reduced tooth 12 is illustrated in greater detail in FIG. 2. Tooth 12 has been reduced to form a subgingival shoulder 13 which ideally is uniformly recessed within the gingival sulcus, i.e. the crevice between the gingiva and the tooth, and therefore closely follows a parallel plane to the contour of the gingival margin 14. As illustrated, the gingival tissue in the labial area of the tooth has been removed for clarity of illustration to reveal the shoulder 13.

With reference to FIGS. 3 and 4, a syringe 5 is provided with an angled head 16 and an adaptor 17, such as a ring nut, screwed to the thread 18 on the head 16 to clamp an impression tube 19 between the head 16 and a return flange 20 on the adaptor 17. The tube 19 has a thickened end flange 21 for such mounting. The head 16 is attachable to the barrel 22 of the syringe 15 by a ring nut 23. With first and second fingers beneath the wings 24 and the thumb depressing the plunger button 25 impression material within the barrel 22 can be forced when required through the impression tube 19.

To avoid perforation, or other injury, to the attachment of the gingiva 27 about the tooth 12 the distal end 28 of the tube 19 must be accurately contoured to the gingival margin about the tooth 12. By this invention this task is performed by the instrument depicted in FIG. 5 and preferably utilizing a stock tube such as that shown in FIG. 6 except that in stock it will not contain the line 38. This tube 19 is preferably composed of any suitable synthetic resinous material, such as nylon, and has a flanged base 21 sufficiently thick to be substantially inflexible for rigid mounting within the adaptor 17 (FIGS. 3 and 4). The tube has an upright tubular stem 29 preferably of thinner material than the base 21 so as to be deformable in its cross-section, but sufficiently thick to be substantially inflexible along its axis. The reason for this construction is to assure firm mounting to the syringe 15 and inflexibility to normal downward pressure by the dentist in the manipulation of the syringe 15 as shown in FIG. 4, while providing for deformation of the walls of the tube to assume a shape generally corresponding to the cross section of the reduced tooth. The dentist will be supplied with a stock of tubes which vary only in the diameter of their stems 29 and he will be required to choose for his use a tube of appropriate diameter.

When the chosen tube 19 is mounted within the syringe 15 by the dentist it will be placed over the reduced tooth 12 and held there in one hand while the instrument of FIG. 5 is applied to scribe a line 38 (see FIG. 6) removed from the distal end 28 on the stem 29 of the tube 19. It will be noted that the instrument 30 is composed of angularly disposed parts 31 and 32 of a handle closely resembling a conventional dental contra-angle handpiece. The distal part 31 as shown in FIG. 4 is disposed substantially horizontally while the other part 32 is upwardly inclined therefrom so that both parts are disposed in a vertical plane. A supporting extension 33 protrudes from the distal end 31 and mounts near its end an operative head 34. The head 34 is rotatable upon a spindle 35 disposed in the same vertical plane as the parts 31 and 32 but normal to the axis of the distal part 21. A graphite stylus 36 depends from the head 34 as does a tracing pin 37, spring biased to its extended position, as shown in FIG. 5. Thus with downward pressure upon the instrument 30 the pin 37 will retract against spring action to allow the point of the stylus 36 to bear against the work-piece, in this case the tube 19.

A contra-angle handpiece is generally accepted by dentists as providing for convenient access to all parts of upper and lower as well as anterior and posterior teeth in the mouth of a patient. Thus, with the use of the present instrument similar dental practice is employed for its manipulation. Rotation of the head 34 provides the dentist with complete flexibility for convenient access to all parts of the patient's mouth and both labial and lingual regions. In use the instrument 30 will be manipulated so that the tracing pin follows the gingival margin 14 about the tooth 12 while the stylus 36 scribes a corresponding line 38 on the tube 19. When tracing is completed in the labial area of the tooth 12 while the syringe 15 is held firm, the instrument 30 will be repositioned at the lingual side of the tooth 12 and thereafter end portion 39 of the stem 29 of the tube 19 beyond line 38 will be removed by cutting by the dentist along the scribed line 38 to form a contoured end matching the gingival margin 14 about the tooth 12. The tube 19 may then be reapplied over the tooth 12 to compress a retraction cord into position, and subsequently after removal of the cord, impression material may be exuded by the syringe 15 in the manner described above in order to obtain an impression of the reduced tooth 12.

The method employed by the dental surgeon in obtaining the desired impression will involve selecting from an available stock a tube 19 of appropriate diameter and attaching it to the syringe 15 by adaptor 17 the syringe 15 being loaded with impression material. The tube 19 is then positioned over the tooth 12 as illustrated in FIG. 4 and brought down to the gingival sulcus and the impression material discharged around the tooth 12 and into the gingival sulcus. As the sulcus fills and excess material exudes from around the distal end 28 of the tube 19 the latter is withdrawn from the tooth 12 while additional impression material is being discharged from the syringe 15. As the tube 19 is fully withdrawn, the tooth 12 is left with a complete covering of impression material, extending into the subgingival area of the tooth 12.

The impression process is repeated with any other prepared teeth in the jaw. To avoid delay, individual impression syringes 15 may be loaded with tubes 19 attached for each tooth to be restored before the impression procedure is initiated. After each prepared tooth has been covered with injected impression material, a full arch impression tray (not shown) loaded with additional impression material is positioned over the teeth and the impression material is allowed to harden. Upon removal of the tray, there is obtained a complete negative of the jaw including detailed impressions of the teeth under restoration from which jacket crowns, bridges, and the like may be prepared in a conventional manner.

The impression tubes 19 may be fabricated of any resilient but relatively inelastic material such as nylon, Teflon, polyethylene, polypropylene, and the like. The tubes 19 are preferably moulded in the desired sizes and may be discarded after use. The syringe 15 are fabricated of rigid plastic and may be either reusable or disposable depending on construction and cost.

Although, the above-described method functions effectively in most instances, deformation of the wall of the tubes 19 can occur under some extreme conditions of use and especially where the impression material is applied under high pressure by the syringe 15. Such wall deformation can cause difficulties in obtaining full penetration of the impression material into the gingival crevasse and effective removal of the tube 19 from the mass of impression material surrounding the reduced tooth.

Figure 2:
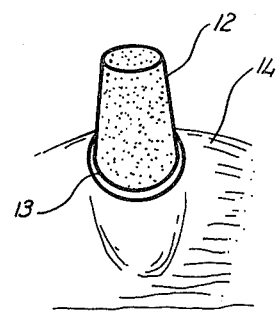
FIG. 2 shows to a larger scale one of said reduced teeth.

As a further embodiment of this invention, therefore, the tube 19 is provided of inflexible material, such as copper, which will have its distal end contoured as described above to match the gingival margin 14 of the reduced tooth 12 (see FIG. 2). The preparation of the distal end 28 of the inflexible tube 19 will be facilitated by the use by the surgeon of the instrument shown in FIG. 5.

Whereas a preferred embodiment has been described in the foregoing passages it should be understood that other forms, modifications and refinements are possible within the scope of this invention. A contra-angle handpiece is defined as an instrument possessing two arms or parts angularly disposed with respect to each other generally in the manner depicted in FIG. 5.

I claim:

1. A hand-held instrument for assisting a dentist in the scribing of a line on a dental impression tube corresponding substantially to the gingival margin at a tooth reduced for a jacket crown, bridgework or like construction, comprising a handle, a distal extension on said handle, a spindle located on said extension and disposed normally thereto, and a head member supported on said spindle, said head member being rotatable with respect to said extension, said head member mounting a sprung tracing pin and a stylus spaced therefrom to enable the dentist to trace said gingival margin with said tracing pin while simultaneously scribing a corresponding line on said dental impression tube.

2. In a method for obtaining a dental impression of a reduced tooth for jacket crown, bridgework or the like construction, which includes providing a tube having an internal diameter substantially corresponding to the diameter of the gingival sulcus in respect of the reduced tooth and having an end contoured to the shape of the gingival margin of the reduced tooth, attaching the opposite end of the tube about the nozzle of a syringe containing impression material, axially applying the tube over the reduced tooth so that its contoured end protrudes into the gingival sulcus of the said reduced tooth, applying impression material from the syringe through said tube until said material exudes from around the contoured end of the tube, retracting said tube while continuing to apply impression material from said syringe until the tube is entirely withdrawn from the reduced tooth, applying a mass of impression material carried in an impression tray over the patients jaw including said reduced tooth, and removing the entire impression material from the patients mouth by withdrawing the impression tray after setting of the impression material, the improvement of providing said tube of a material and thickness to be at least axially substantially inflexible, and of firstly scribing thereon a line parallel to said gingival margin while positioning the tube over the reduced tooth and subsequently trimming the end of said tube to said line to form an accurately contoured end on said tube.

3. A method for producing by a dentist an impression tube to be used in the production of a dental impression of a tooth reduced for a jacket crown, bridgework and like constructions, comprising selecting from a stock of tubes, all of which are substantially inflexible at least longitudinally, a single tube of a diameter corresponding to the gingival sulcus of said tooth, affixing said tube upon a syringe being held in one hand by the dentist to provide support for said tube about said tooth with its distal end adjacent the gingiva, scribing a line on the outer wall of said tube which is substantially parallel to the gingival margin of the tooth, and removing that portion of the tube at the distal end beyond said scribed line to create a contour on said tube end which substantially corresponds to said gingival margin.

4. The method of claim 3, wherein said tube remains mounted upon the syringe during said removal of said end portion, and is replaced about said tooth with its contoured end matching the gingival margin contour and inserted into the gingival sulcus whereby impression material in said syringe when exuded is confined by the tube about said tooth and the subgingival shoulder thereon.

5. The method of claim 4, wherein said line is scribed by an instrument held in one hand by the dentist and which includes a stylus for scribing and a tracing pin spaced therefrom, and the instrument is moved by the dentist around the tube while said tracing pin is caused to follow the gingival margin.

* * * * *